(12) United States Patent
Liu et al.

(10) Patent No.: US 10,940,118 B2
(45) Date of Patent: Mar. 9, 2021

(54) NANOPARTICLES AND METHODS OF PRODUCING THE SAME

(71) Applicant: THE BOARD OF TRUSTEES OF THE UNIVERSITY OF ILLINOIS, Urbana, IL (US)

(72) Inventors: Ying Liu, Clarendon Hills, IL (US); Zaijie Wang, Oak Park, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 14/903,568

(22) PCT Filed: Jul. 11, 2014

(86) PCT No.: PCT/US2014/046418
§ 371 (c)(1),
(2) Date: Jan. 7, 2016

(87) PCT Pub. No.: WO2015/006735
PCT Pub. Date: Jan. 15, 2015

(65) Prior Publication Data
US 2016/0166513 A1 Jun. 16, 2016

Related U.S. Application Data

(60) Provisional application No. 61/845,228, filed on Jul. 11, 2013.

(51) Int. Cl.
| | | |
|---|---|---|
| *A61K 9/51* | (2006.01) | |
| *A61K 31/155* | (2006.01) | |
| *A61K 31/566* | (2006.01) | |
| *A61K 31/7036* | (2006.01) | |
| *A61K 31/18* | (2006.01) | |
| *A61K 31/7048* | (2006.01) | |
| *A61K 31/704* | (2006.01) | |
| *A61K 31/12* | (2006.01) | |
| *A61K 31/485* | (2006.01) | |
| *A61K 38/00* | (2006.01) | |

(52) U.S. Cl.
CPC .......... *A61K 9/5153* (2013.01); *A61K 9/5192* (2013.01); *A61K 31/12* (2013.01); *A61K 31/155* (2013.01); *A61K 31/18* (2013.01); *A61K 31/485* (2013.01); *A61K 31/566* (2013.01); *A61K 31/704* (2013.01); *A61K 31/7036* (2013.01); *A61K 31/7048* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 6,007,845 A | * | 12/1999 | Domb | A61K 9/5153 424/451 |
| 7,667,004 B2 | | 2/2010 | Zhong et al. | |
| 2003/0129239 A1 | * | 7/2003 | Goldshtein | A61K 9/5161 424/486 |
| 2007/0122440 A1 | * | 5/2007 | Macosko | A61K 9/5153 424/405 |
| 2009/0087494 A1 | | 4/2009 | Kompella et al. | |
| 2011/0091560 A1 | * | 4/2011 | Smith | A61K 9/5153 424/489 |
| 2011/0237686 A1 | * | 9/2011 | Ng | A61K 9/19 514/772.1 |
| 2011/0237748 A1 | * | 9/2011 | Podobinski | A61J 1/00 525/56 |
| 2013/0122058 A1 | * | 5/2013 | Chow | A61K 9/146 424/400 |

FOREIGN PATENT DOCUMENTS

WO WO-2013/063279 A1 5/2013

OTHER PUBLICATIONS

Hu, J., et al., "Continuous and scalable process for water-redispersible nanoformulation of poorly aqueous soluble APIs by antisolvent precipitation and spray-drying", Int. J. Pharm., 2011, pp. 198-204.*
Zhu, Z., et al., "Polyelectrolyte Stabilized Drug Nanoparticles via Flash Nanoprecipitation: A Model Study With b-Carotene", Pharmaceutical Nanotechnology, 2010, pp. 4295-4306.*
Mejia-Ariza, R., "Design, Synthesis, and Characterization of Magnetite Clusters using a Multi Inlet Vortex Mixer" Virginia Polytechnic Thesis, pp. 1-101, (Year: 2010).*
Valencia, P.M., et al., "Single-Step Assembly of Homogenous Lipid Polymeric and Lipid Quantum Dot Nanoparticles Enabled by Microfluidic Rapid Mixing", ACS Nano, pp. 1671-1679 (Year: 2010).*
Banerjee et al. "Enhanced Oral Bioavailability of the Hydrophobic Chemopreventive Agent (Sr13668) in Beagle Dogs," Current Pharmaceutical Biotechnology, 14:464-469 (2013).

(Continued)

*Primary Examiner* — Michael G. Hartley
*Assistant Examiner* — Lance W Rider
(74) *Attorney, Agent, or Firm* — Marshall, Gerstein & Borun LLP

(57) ABSTRACT

The present disclosure provides methods and compositions related to nanoparticles comprising an encapsulated hydrophobic drug. The methods described herein provide nanoparticles having a small size and a narrow size distribution.

18 Claims, 14 Drawing Sheets

(56) References Cited

OTHER PUBLICATIONS

Shen "Orally Administered Nanocurcumin to Attenuate Morphine Tolerance: Comparison between Negatively Charged PLGA and Partially and Fully PEGylated Nanoparticles," Mol. Pharmaceutics 10:4546-4551 (2013).
Shen et al. "Self-assembling process of flash nanoprecipitation in a multi-inlet vortex mixer to produce drug-loaded polymeric nanoparticles," J Nanopart Res 13:4109-4120 (2011).
International preliminary report on patentability from PCT/US2014/46418 dated Jan. 12, 2016.
International search report from PCT/US2014/46418 dated Oct. 27, 2014.
Shen et al., "Enhanced Oral Bioavailability of a Cancer Preventive Agent (SR13668) by Employing Polymeric Nanoparticles with High Drug Loading," J Pharm Sci, 101(10):3877-3885 (2012).
Written opinion from PCT/US2014/46418 dated Oct. 27, 2014.

* cited by examiner

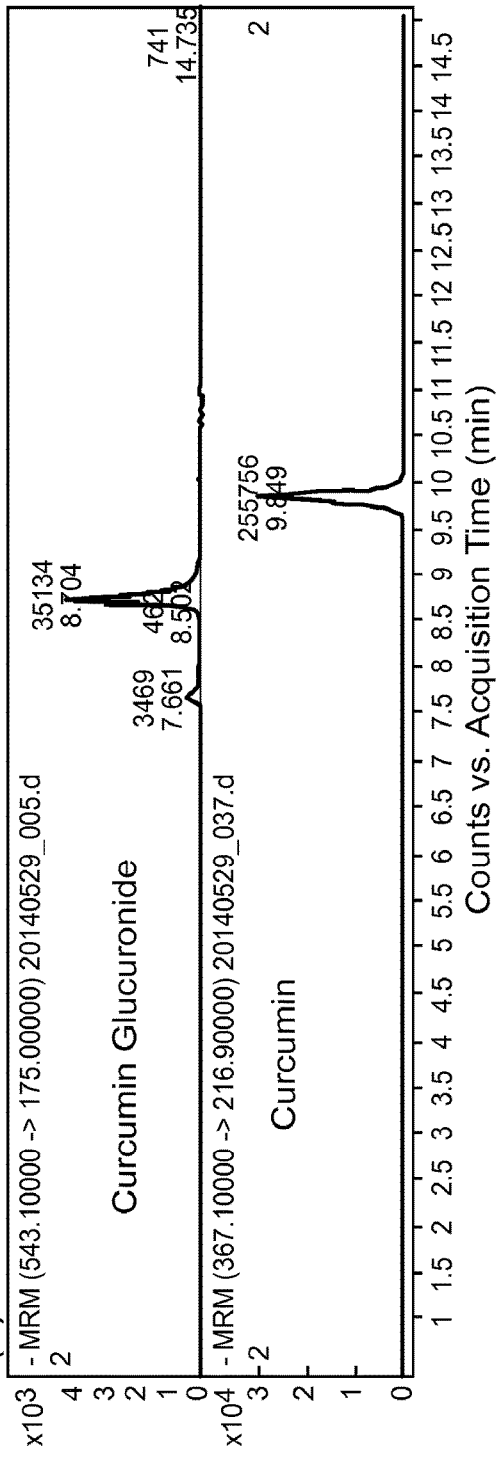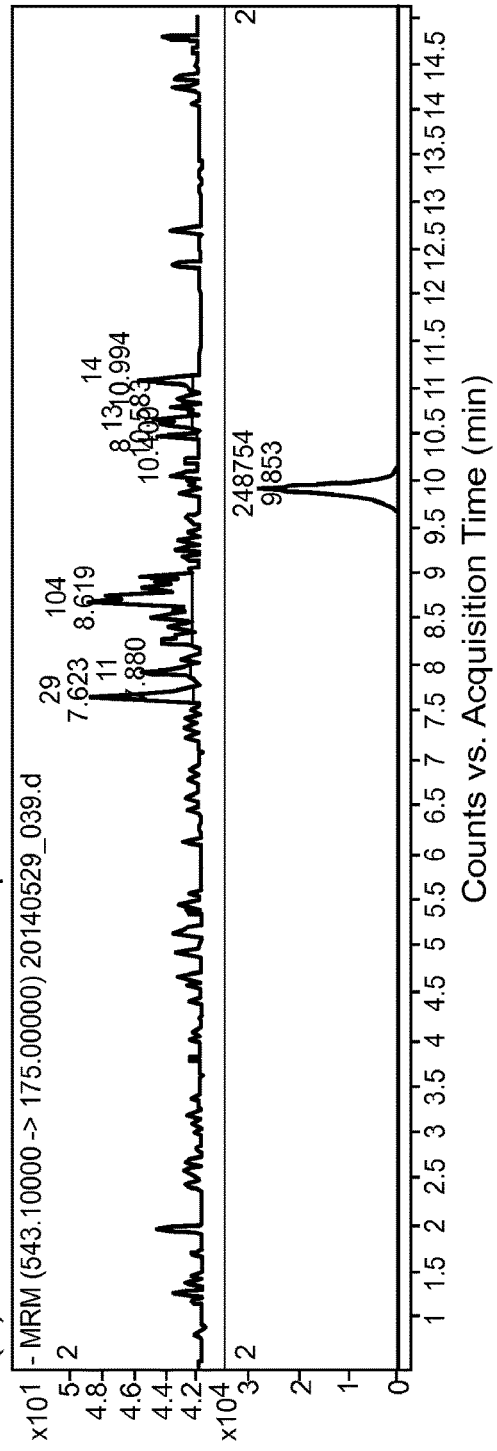
Figure 10A
Figure 10B

NANOPARTICLES AND METHODS OF PRODUCING THE SAME

CROSS REFERENCE TO RELATED APPLICATIONS

This application is a U.S. National Phase of PCT/US2014/046418, filed Jul. 11, 2014, which claims the priority benefit under 35 U.S.C. § 119(e) of U.S. Provisional Patent Application Number 61/845,228, filed Jul. 11, 2013, the disclosures of which are incorporated herein by reference in their entirety.

FIELD OF THE INVENTION

The present subject matter relates generally to polymeric nanoparticles and methods of producing nanoparticles. More specifically, the present invention relates to bioavailable nanoparticles encapsulating a hydrophobic drug (e.g., curcumin) and a continuous and scalable process to reproducibly generate stable nanoparticles with controlled size distribution and high drug loading.

BACKGROUND OF THE INVENTION

Poor aqueous solubility presents one of the major limiting factors for sufficient oral absorption and bioavailability for many therapeutic leads in the current drug discovery pipeline. Nearly 40% of the pharmaceutical compounds on the market and 90% of the newly developed compounds are hydrophobic, and therefore difficult to deliver and to maintain sufficient bioavailability.

Nano-sizing is recently of great interest to increase hydrophobic drug solubility and therefore bioavailability, because of the large surface area of the nanoparticles and enhanced solubility based on the curvature of the particles. Among various types of nano-materials, polymeric nanoparticles have the advantages of relatively high biocompatibility, stability, and flexibility to conjugate with ligands on their surface for targeted drug delivery.

A few methods have been developed to prepare polymeric nanoparticles encapsulating hydrophobic drugs, such as supercritical processing, emulsification, sonication and nanoprecipitation. However, limited drug loading (<15%) has been an issue for most polymeric particles prepared by above conventional procedures, despite the ideal hydrophobic interaction between the drug and the hydrophobic block of the copolymer.

After nanoparticles are made, it is critical to keep their long-term stability. When nanoparticles are suspended in solutions, the size of the particles keeps grow due to aggregation, secondary crystallization, and Ostwald ripening. Moreover, producing polymeric nanoparticles encapsulating hydrophobic drug compounds in a scalable and reproducible manner is the key for nanoparticles to be practically applied as novel medicine.

Opioids, such as morphine, are widely used in the clinical management of acute and chronic pains. Drug tolerance (a decreased effect of a drug with repeated administration) and dependence (inability to stop using a drug even with strong desire to do so) are two of the major issues associated with opioids, which greatly limit their clinical applications.

*Curcuma longa* is a yellow-colored traditional herb which has been used for thousands of years in Asia for food flavoring, preservation, coloring material, as well as medicinal use. Curcumin [1,7-bis-(4-hydroxy-3-methoxyphenyl)-1,6-heptadiene-3,5-dione] is the active constituent of *Curcuma longa*. It was recently found to have a wide spectrum of pharmacological activities, including antioxidant, cancer chemopreventive, anti-inflammatory, neuro-protective and antinociceptive actions. In recent years, a preliminary report suggested that chronic dose of large amount of curcumin (100 mg/kg) might attenuate morphine tolerance. This opens a new window for curcumin be potentially used to alleviate morphine tolerance in patients with chronic pain and on long-term opioid therapy. However, the applications of curcumin have been hindered by its poor aqueous solubility, relatively low bioavailability, high rate of metabolism and rapid elimination and clearance from the body. Although curcumin has been shown to be safe in many animal and human studies even at relatively high dosages, recent studies indicate that some of the effects (such as inhibition of proteasomal function and potentiation of huntingtin toxicity) of high dose curcumin are clearly toxic and undesirable beyond its use in cancer therapy. Biphasic effect of curcumin on morphine tolerance and body weight loss on mice study were also observed.

Accordingly, a need exists for a bioavailable curcumin nanoparticles and a continuous and scalable process to reproducibly generate stable nanoparticles with controlled size distribution and high drug loading as described and claimed herein.

BRIEF SUMMARY OF THE INVENTION

Disclosed herein are methods and compositions related to nanoparticles comprising an encapsulated hydrophobic drug. The methods described herein provide nanoparticles having a small size and a narrow size distribution.

The present disclosure formulated a representative hydrophobic drug, curcumin, into stable nanoparticle suspensions (nano-curcumin) to overcome its relatively low bioavailability, high rate of metabolism and rapid elimination and clearance from the body and provides that nano-curcumin [1,7-bis-(4-hydroxy-3-methoxyphenyl)-1,6-heptadiene-3,5-dione] alleviates morphine tolerance and dependence. The two types of stable polymeric nanoparticles poly(lactic-co-glycolic acid) (PLGA) and poly(ethylene glycol)-b-poly(lactic acid) (PEG-b-PLA) and the hybrid of the two were generated using flash nanoprecipitation integrated with spray drying. The optimized formulation has high drug loading (more than 47%), small particles size with narrow distribution, and controlled surface properties. Mice behavioral studies (tail-flick, hot-plate, and withdrawal jump tests) were conducted to verify the effects of nano-curcumin on attenuating morphine tolerance and dependence. Significant analgesia was observed in mice during both tail-flick and hot plate tests using orally administrated nano-curcumin following subcutaneous injection of morphine. However, unformulated curcumin at the same concentration showed minimal effect. Negatively charged PLGA nanoparticles compared to PEGylated ones show better functionality.

The enhanced oral bioavailability of a hydrophobic drug compound was demonstrated in mice and beagle dogs.

An advantage of the nanoparticles of the disclosure (e.g., curcumin nanoparticles) is that the optimized formulation has high drug loading of at least 30%, or at least 47%.

Another advantage of the nanoparticles of the disclosure (e.g., curcumin nanoparticles) is that they have small particle size with narrow distribution.

Another advantage of the nanoparticles of the disclosure (e.g., curcumin nanoparticles) is that they have controlled surface properties.

A further advantage of the nanoparticles of the disclosure (e.g., curcumin nanoparticles) is that they may be developed using a continuous and scalable process.

Yet another advantage of the nanoparticles of the disclosure (e.g., curcumin nanoparticles) is that they enhance oral bioavailability of a hydrophobic drug compound was demonstrated in mice.

The present disclosure provides, in one aspect, a method for producing a nanoparticle comprising: (a) dissolving at least one hydrophobic bioactive agent and at least one biocompatible polymer in an organic solvent; (b) mixing the resultant mixture in the organic solvent under shear conditions with one or more antisolvent(s) to produce the nanoparticle; (c) adding an additive to the mixture; and (d) drying the mixture. In some embodiments, the method further comprises resuspending the nanoparticle in an aqueous or in an organic solution.

In some embodiments, the nanoparticle further comprises a marker. In various embodiments, the marker is a fluorescent dye (e.g., Nile Red), an organic or inorganic dye, an inorganic nano-crystal/particle (such as, without limitation, upconverting phosphors, gold particles, and iron oxide particles), or a colloid.

In various embodiments, the additive is selected from the group consisting of a sugar-type molecule, a sugar alcohol, an amino acid, a surfactant, and a biocompatible polymer. The sugar-type molecule is, in various embodiments, selected from the group consisting of glucose, fructose, trehalose, sucralose, and lactose. The sugar alcohol is, in various embodiments, selected from the group consisting of glycerol, lactitol, xylitol, and sorbitol. The amino acid is, in various embodiments, selected from the group consisting of leucine, lysine, glycine, threonine, and valine. The surfactant is, in various embodiments, selected from the group consisting of a fatty acid, a lipopeptides, and a glycolipid. The biocompatible polymer is, in various embodiments, selected from the group consisting of polyvinyl alcohol, polyvinylpyrrolidone, PLURONIC® (polyethylene glycol-polypropylene glycol-polyethylene glycol), and polyethylene glycol.

In further embodiments, the weight ratio of additive to nanoparticle is from about 1:1 to about 300:1. In further embodiments, the weight ratio of additive to nanoparticle is from about 1:1 to about 250:1, or from about 1:1 to about 200:1, from about 1:1 to about 150:1, from about 1:1 to about 100:1, from about 1:1 to about 50:1, from about 1:1 to about 40:1, from about 1:1 to about 30:1, from about 1:1 to about 20:1, or from about 1:1 to about 10:1. In still further embodiments, the ratio of additive to nanoparticle is at least 1:1, or at least 2:1, or at least 3:1, or at least 4:1, or at least 5:1, or at least 10:1, or at least 15:1, or at least 20:1, or at least 25:1, or at least 50:1, or at least 75:1, or at least 100:1, or at least 150:1, or at least 200:1, or at least 250:1, or at least 500:1. In still further embodiments, the weight ratio of additive to nanoparticle is about 1:1, or about 2:1, or about 3:1, or about 4:1, or about 5:1, or about 10:1, or about 15:1, or about 20:1, or about 25:1, or about 50:1, or about 75:1, or about 100:1, or about 150:1, or about 200:1, or about 250:1, or about 500:1.

In another aspect, the disclosure provides a nanoparticle composition formed by any of the methods disclosed herein.

In yet another aspect of the disclosure, a scalable and continuous method for manufacturing stable polymeric nanoparticles encapsulating a hydrophobic compound is provided, comprising: (a) dissolving at least one hydrophobic bioactive agent and at least one biocompatible polymer in one or more organic solvents, and (b) mixing the resultant mixture in the one or more organic solvent(s) under shear conditions with one or more antisolvent(s) to form nanoparticles. In some embodiments, the method further comprises the steps of nanoparticle characterization, spray drying/freeze drying, and re-suspension.

In additional embodiments, at least one marker is used. In some embodiments, the hydrophobic compound is selected from the group consisting of tobramycin, digoxin, estrone, glyburide, metformin, and doxorubicin.

In another aspect of the disclosure, a composition comprising a nanoparticle is provided that comprises a hydrophobic drug, wherein the drug is encapsulated by a polymer, and wherein the drug loading of the nanoparticle is at least about 30%. In some embodiments, the polymer is poly (lactic-co-glycolic acid) (PLGA). In some embodiments, the polymer is poly(ethylene glycol)-b-poly(lactic acid) (PEG-b-PLA). In further embodiments, the composition comprises a plurality of nanoparticles, wherein the plurality of nanoparticles has a defined particle size distribution.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE INVENTION

Figure 1:
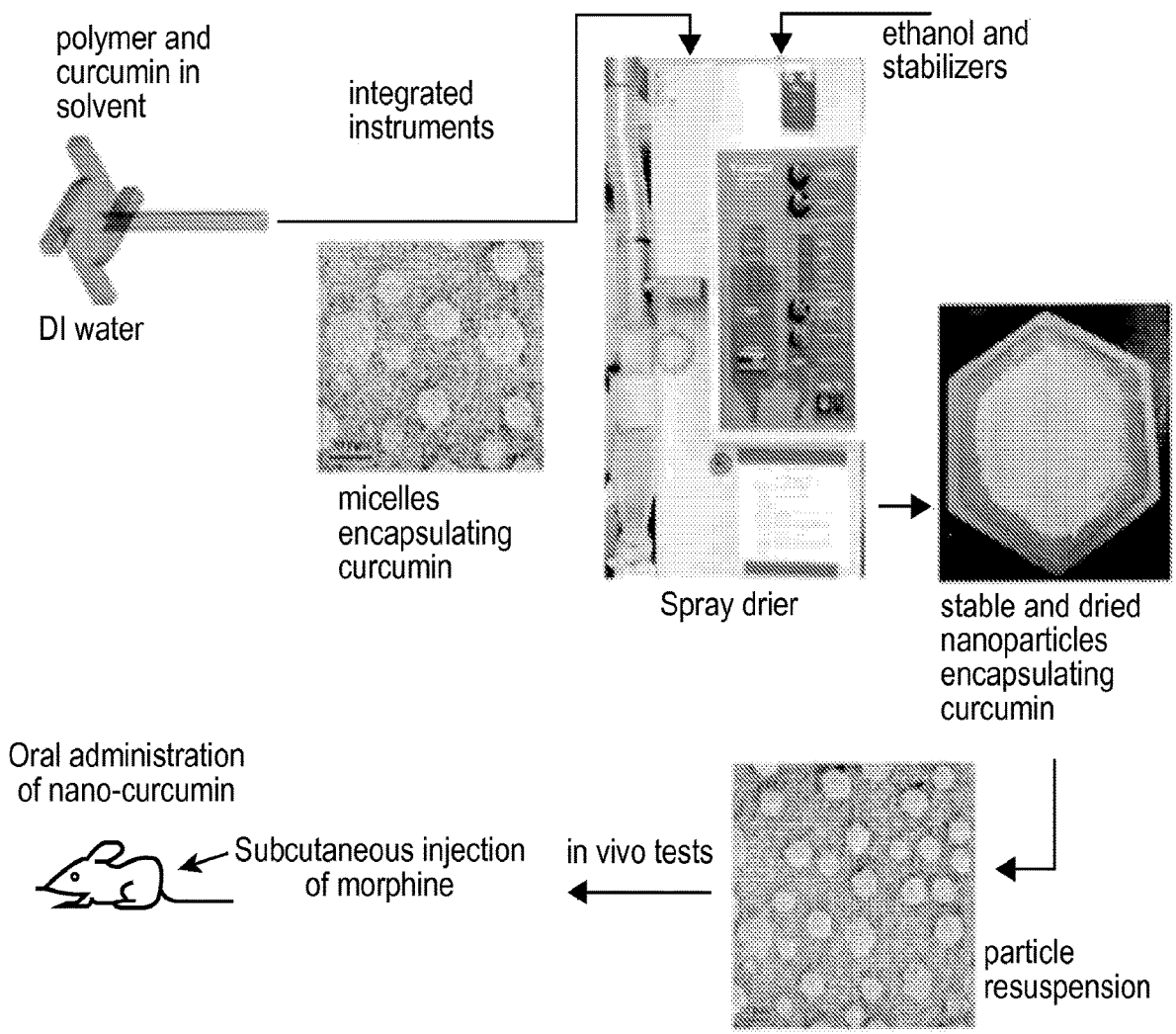
FIG. 1. Illustrate the scalable, continuous formation process and in vitro and in vivo characterization for nano-curcumin.

In general, the disclosure provides a polymeric nanoparticle encapsulating a hydrophobic drug. The nanoparticles produced by the methods disclosed herein exhibit a small particle size and narrow size distribution, making them useful in a wide range of applications as discussed herein.

In one aspect, the present disclosure formulated hydrophobic curcumin into stable nanoparticle suspensions (nano-curcumin) to overcome its relatively low bioavailability, high rate of metabolism and rapid elimination and clearance from the body and provides that nano-curcumin [1,7-bis-(4-hydroxy-3-methoxyphenyl)-1,6-heptadiene-3,5-dione] alleviates morphine tolerance and dependence. The two types of stable polymeric nanoparticles poly(lactic-co-glycolic acid) (PLGA) and poly(ethylene glycol)-b-poly(lactic acid) (PEG-b-PLA) and the hybrid of the two were generated using flash nanoprecipitation integrated with spray drying. The optimized formulation has high drug loading (47%), small particles size with narrow distribution, and controlled surface properties.

The disclosure contemplates that the weight ratio of polymer to drug is from 10:1 to 1:10.

Definitions

The terminology used herein is for the purpose of describing particular embodiments only and is not intended to be limiting. As used in the specification and the appended claims, the singular forms "a," "and" and "the" include plural references unless the context clearly dictates otherwise.

When a group of substituents is disclosed herein, it is understood that all individual members of that group and all subgroups, are disclosed separately. When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated. All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising," "consisting essentially of" and "consisting of" may be replaced with either of the other two terms. The invention illustratively described herein suitably may be practiced in the absence of any element or elements, limitation or limitations which is not specifically disclosed herein.

As used herein, an "antisolvent" is any solvent that does not dissolve the drug(s) and the polymer(s). For a hydrophobic drug, an antisolvent is, for example and without limitation, an aqueous solution such as water. Ethanol is another non-limiting example of a solution that can be used as an antisolvent. Combinations of antisolvents (for example, ethanol and water) are also contemplated by the disclosure.

As used herein, "shear conditions" refer to the rapid mixing of the at least one hydrophobic bioactive agent and at least one biocompatible polymer with an organic solvent. By way of example, the mixing occurs as quickly as 1 or 1.5 milliseconds.

As used herein, a "hydrophobic bioactive agent" is any hydrophobic agent for which encapsulation is desirable. In some embodiments, the hydrophobic bioactive agent is a hydrophobic drug. In further embodiments, the hydrophobic bioactive agent is a curcuminoid including curcumin and synthetic derivatives thereof. "Hydrophobic" as used herein is understood to mean that the solubilities in aqueous solutions for the active agents contemplated in the present disclosure are "sparingly" (30 to 100 parts solvent to dissolve 1 part solute, or active agent), "slightly" (100 to 1000 parts solvent to dissolve 1 part solute), "very slightly" (1000 to 10,000 parts solvent to dissolve 1 part solute) soluble, or "practically insoluble" (more than 10,000 parts solvent to dissolve 1 part solute) [see, e.g., The United States Pharmacopeia (USP 24/NF 19), United States Pharmacopeial Convention, Inc., 2000, incorporated by reference herein in its entirety]. In various embodiments, therapeutic agents described in U.S. Pat. No. 7,667,004 (incorporated by reference herein in its entirety) are contemplated for use in the compositions and methods disclosed herein and include, but are not limited to, alkylating agents, antibiotic agents, antimetabolic agents, hormonal agents, plant-derived agents, and biologic agents.

Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (e.g., carboplastin and cisplatin).

Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin, and rifampicin.

Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, imatinib mesylate (or GLEEVEC®), and gemcitabine.

Examples of hormonal agents include, but are not limited to, synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone.

Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), camptothecin compounds (e.g., 20(S) camptothecin, topotecan, rubitecan, and irinotecan), taxanes (e.g., paclitaxel and docetaxel).

Examples of biologic agents include, but are not limited to, immuno-modulating proteins such as cytokines, monoclonal antibodies against tumor antigens, tumor suppressor genes, and cancer vaccines. Examples of interleukins that may be used in conjunction with the compositions and methods of the present invention include, but are not limited to, interleukin 2 (IL-2), and interleukin 4 (IL-4), interleukin 12 (IL-12). Examples of interferons that may be used in conjunction with the compositions and methods of the present invention include, but are not limited to, interferon α, interferon β and interferon γ. Examples of cytokines include, but are not limited to, erythropoietin (epoietin α), granulocyte-CSF (filgrastin), and granulocyte, macrophage-CSF (sargramostim). Other immuno-modulating agents other than cytokines include, but are not limited to bacillus Calmette-Guerin, levamisole, and octreotide.

Curcumin Nanoparticles

The present invention claims curcumin nanoparticles comprising PLGA and PEG-b-PLA nanoparticles encapsulating curcumin, where the drug loading is at least 47%. The hydrophobic curcumin is formulated into stable nanoparticle suspensions (nano-curcumin) to overcome its relatively low bioavailability, high rate of metabolism and rapid elimination and clearance from the body and provides that nano-curcumin [1,7-bis-(4-hydroxy-3-methoxyphenyl)-1,6-heptadiene-3,5-dione] alleviates morphine tolerance and dependence. The two types of stable polymeric nanoparticles poly(lactic-co-glycolic acid) (PLGA) and poly(ethylene glycol)-b-poly(lactic acid) (PEG-b-PLA) and the hybrid of the two were generated using flash nanoprecipitation integrated with spray drying. The optimized formulation has high drug loading (47%), small particles size with narrow distribution, and controlled surface properties.

Experimental Section

PLGA (acid terminated; PLA:PGA 50:50 w/w; Mw 7000-17000), curcumin, tetrahydrofuran (THF), dimethyl sulfoxide (DMSO), ethanol, leucine, trehalose and naloxone were purchased from Sigma-Aldrich (St Louis, Mo.). Methyl tert-butyl ether (MTBE) (HPLC grade) was purchased from Fisher Scientific (Pittsburgh, Pa.). Morphine was purchased from Hospira (Lake Forest, Ill.). Poly(ethylene glycol)-b-poly(lactic acid) (PEG-b-PLA) (MW 5000-b-6700) was purchased from Polymer Source (Dorval, Canada). Unless otherwise stated, all chemicals were purchased at standard grades and used as received.

Preparation and Size Characterization of Nanoparticle Suspensions

As shown in FIG. 1, a method for producing curcumin nanoparticles comprises dissolving at least one hydrophobic bioactive agent and at least one biocompatible polymer in one organic solvent or different organic solvents if the polymers and the drug do not dissolve in the same one, and rapidly mixing the resultant mixture in the organic solvent(s) with an antisolvent to form nanoparticles. The scalable and continuous method may include steps of nanoparticle characterization, spray drying/freeze drying, and re-suspension. At least one marker may be used using this method. In various embodiments, the marker is a fluorescent dye (e.g., Nile Red), an organic or inorganic dye, an inorganic nanocrystal/particle (such as, without limitation, upconverting phosphors, gold particles, and iron oxide particles), or a colloid.

Accordingly, in some aspects an organic solvent is used in the process to dissolve hydrophobic compounds. In some embodiments, the organic solvents are completely evaporated after the spray/freeze dry process; thus, polar and non-polar solvents with low boiling points are preferred. In further embodiments, the organic solvent is mixable with water/aqueous solutions. Organic solvents contemplated for use by the disclosure include, but are not limited to, acetic acid, acetone, acetonitrile, dimethoxy ethane (DME), dimethyl formamide (DMF), ethanol, ethyl acetate, methanol, methyl t-butyl ether (MTBE), tetrahydrofuran (THF), and propanol.

Polymer to Drug Ratios. With a higher polymer to drug ratio, the average size of the particles are smaller and particles are more stable when suspended in aqueous solutions. However, increasing polymer to drug ratio reduces the loading of the drug. The disclosure contemplates that ratios of polymer to drug from at least about 10:1 to at least about 1:10, or from at least about 9:1 to at least about 1:10, or from at least about 8:1 to at least about 1:10, or from at least about 7:1 to at least about 1:10, or from at least about 6:1 to at least about 1:10, or from at least about 5:1 to at least about 1:10, or from at least about 4:1 to at least about 1:10, or from at least about 3.1 to at least about 1:10, or from at least about 2:1 to at least about 1:10, or from at least about 1:1 to at least about 1:10, or from at least about 10:1 to at least about 1:9, or from at least about 10:1 to at least about 1:8, or from at least about 10:1 to at least about 1:7, or from at least about 10:1 to at least about 1:6, or from at least about 10:1 to at least about 1:5, or from at least about 10:1 to at least about 1:4, or from at least about 10:1 to at least about 1:3, or from at least about 10:1 to at least about 1:2, or from at least about 10:1 to at least about 1:1, are useful in the compositions and methods described herein. In further embodiments, the disclosure contemplates a ratio of polymer to drug that is at least about 1:1, or at least about 2:1, or at least about 3:1, or at least about 4:1, or at least about 5:1, or at least about 6:1, or at least about 7:1, or at least about 8:1, or at least about 9:1, or at least about 10:1, or at least about 1:2, or at least about 1:3, or at least about 1:4, or at least about 1:5, or at least about 1:6, or at least about 1:7, or at least about 1:8, or at least about 1:9, or at least about 1:10, are useful in the compositions and methods described herein.

In the example shown in FIG. 1, PLGA and PEG-b-PLA nanoparticles encapsulating curcumin were generated by using a multi-inlet vortex mixer (MIVM). Among the four inlet streams, stream 1 was 0.2 wt % polymer and 0.2 wt % curcumin dissolved in THF. The other three inlet streams were Millipore water as an anti-solvent to precipitate the drug compound and polymers. The volumetric flow rate of streams 1 and 2 was 6 mL/min and it was 54 mL/min for streams 3 and 4.

The disclosure contemplates that multi-inlet design of the reactor can, in various embodiments, provide additional flexibility if one or more drug(s) and one or more polymer(s) cannot be dissolved in the same solvent. For example and without limitation, the disclosure contemplates three schemes for a multi-inlet design—(a) same stream; (b) next stream; and (c) opposite stream (see FIG. 11).

Figure 11:
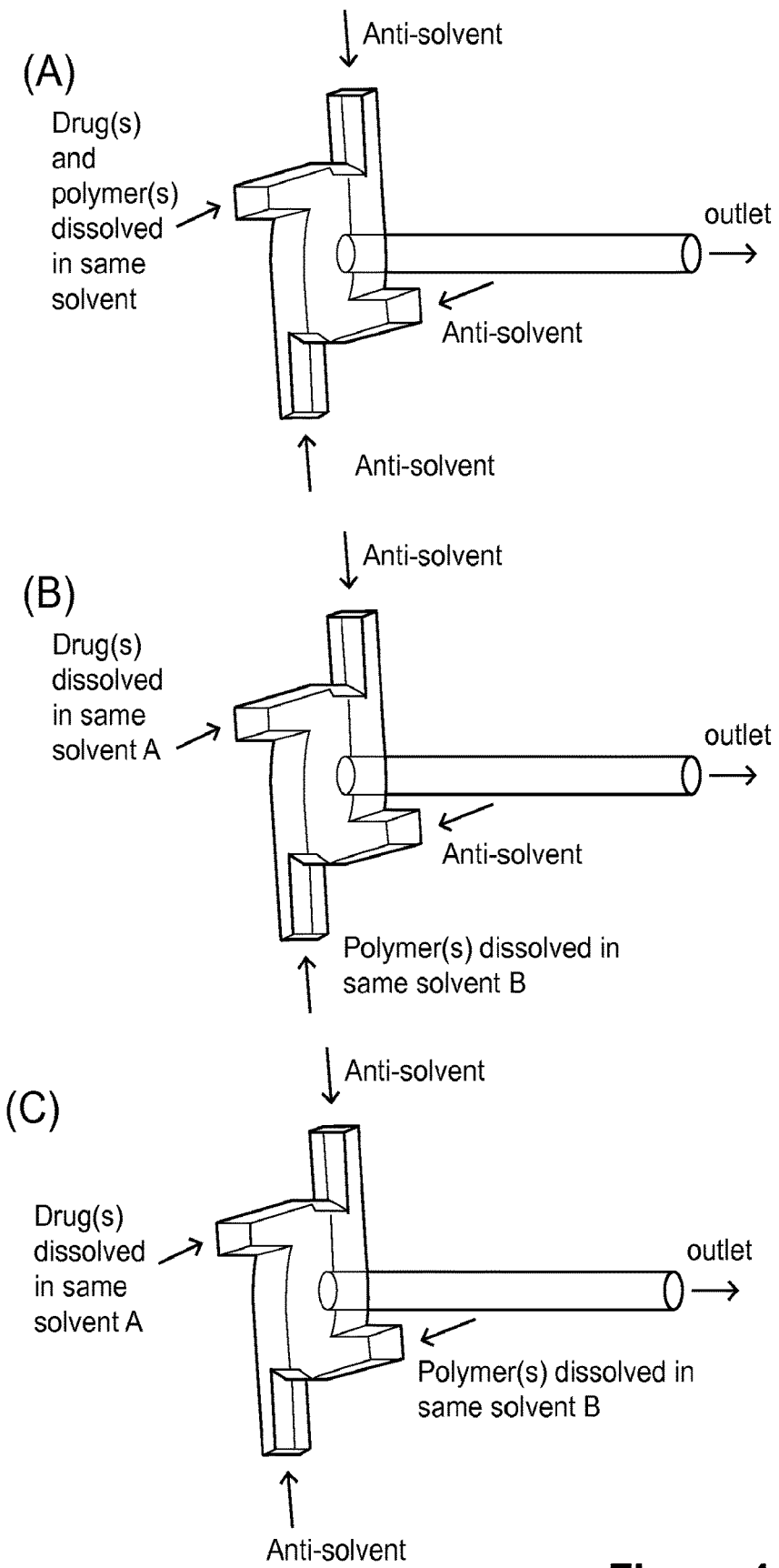
FIG. 11 depicts (A) Same stream: drug(s) and polymer(s) are dissolved in the same organic solvent and mixed with the anti-solvent (such as water or aqueous solutions). (B) Next stream: drug(s) are dissolved in solvent A and polymer(s) are dissolved in solvent B (which has to be the good solvent for all the blocks of the polymer). The two organic streams are placed next to each other and mixed with the rest streams of anti-solvent. (C) Opposite streams: drug(s) are dissolved in solvent A and polymer(s) are dissolved in solvent B. The two organic streams are placed opposite to each other and mixed with the rest streams of anti-solvent.
Figure 12:
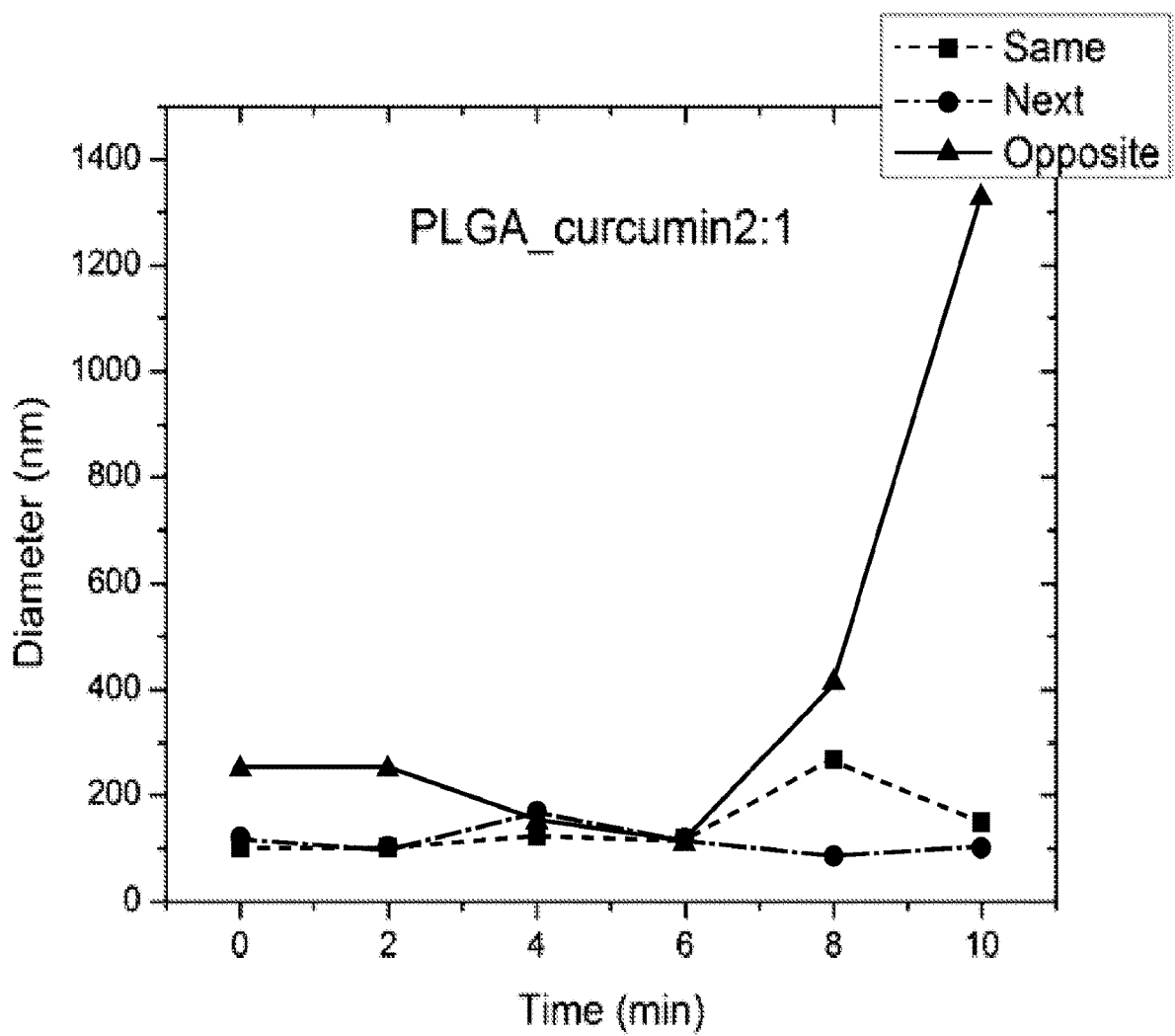
FIG. 12 depicts the particle size and stability characterized for curcumin and PLGA nanoparticles placed in the same (squares), next (circles), and opposite (triangles) inlet streams of the reactor. In this example the ratio of PLGA and curcumin was 2:1.

The disclosure further contemplates that various drugs or polymers can be separated in additional inlet streams (see, e.g., FIG. 11). The resultant particles are similar for the same stream and next stream in terms of the initial particle size and stability for about the first 10 minutes. When placed in opposite streams, the resultant particles are relatively bigger.

Nanoparticle size distributions were measured by dynamic light scattering (DLS) (Malvern, Zetasizer Nano ZS90, Worcestershire, UK). The particle sizes were reported as the intensity-weighted radius. Viscosity and refractive index of the solvent were set to be 0.933 cP and 1.333, respectively.

Nanoparticles can range in size from about 1 nm to about 500 nm in mean diameter, about 1 nm to about 450 nm in mean diameter, about 1 nm to about 400 nm in mean diameter, about 1 nm to about 350 nm in mean diameter, about 1 nm to about 300 nm in mean diameter, about 1 nm to about 250 nm in mean diameter, about 1 nm to about 200 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, about 1 nm to about 10 nm in mean diameter. In other aspects, the size of the nanoparticles is from about 100 nm to about 500 nm (mean diameter), from about 100 to about 450 nm, from about 100 to about 400 nm, from about 100 to 350 nm, from about 100 to about 300 nm, or about 100 to about 250 nm. The size of the nanoparticles is from about 50 nm to about 500 nm (mean diameter), from about 50 to about 450 nm, from about 50 to about 400 nm, from about 50 nm to about 350 nm, from about 50 nm to about 300 nm, from about 50 nm to about 250 nm, from about 50 nm to about 200 nm, from about 50 nm to about 150 nm, or from about 50 nm to about 100 nm. In further embodiments, the size of the nanoparticles is at least about 1 nm, at least about 5 nm, at least about 10 nm, at least about 20 nm, at least about 50 nm, at least about 100 nm, at least about 150 nm, at least about 200 nm, at least about 250 nm, at least about 300 nm, at least about 350 nm, at least about 400 nm, at least about 420 nm, at least about 430 nm, at least about 440 nm, at least about 450 nm, or at least about 500 nm. In further embodiments, the size of the nanoparticles is less than about 50 nm, less than about 100 nm, less than about 150 nm, less than about 200 nm, less than about 250 nm, less than about 300 nm, less than about 350 nm, less than about 400 nm, less than about 420 nm, less than about 430 nm, less than about 440 nm, less than about 450 nm, or less than about 500 nm.

The size of the nanoparticles used in a method varies as required by their particular use or application.

The definition of drug loading (DL) and encapsulation efficiency (EE) were defined as $$DL\ (\%) = \frac{\left(\begin{array}{c}\text{Amount of } SR13668 \text{ encapsulated in}\\ \text{nanoparticles smaller than 450 nm}\end{array}\right)}{\text{(Total weight of nanoparticles)}} \times 100\%$$

and $$EE\ (\%) = \frac{\begin{array}{c}\text{Amount of } SR13668 \text{ encapsulated in}\\ \text{nanoparticles smaller than 450 nm}\end{array}}{\text{Feeding amount of } SR13668} \times 100\%$$

respectively. Drug loading of curcumin in nanoparticles was quantified by UV-Vis spectrophotometer measurements at the absorbance wavelength of 435 nm, after the samples were spray dried and then redissolved in DMSO at a solid concentration of 2 mg/mL.

Drug loading of nanoparticles that are produced according to any of the methods described herein is, in various embodiments, at least about 30%, or at least about 35%, or at least about 40%, or at least about 45%, or at least about 47%, or at least about 48%, or at least about 49%, or at least about 50%, or at least about 51%, or at least about 52%, or at least about 53%, or at least about 54%, or at least about 55%, or at least about 56%, or at least about 57%, or at least about 58%, or at least about 59%, or at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%. In further embodiments, drug loading of nanoparticles that are produced according to any of the methods described herein is from about 30% to about 90%, or from about 40% to about 90%, or from about 40% to about 80%, or from about 40% to about 70%, or from about 40% to about 60%, or from about 40% to about 50%, or from about 50% to about 90%, or from about 50% to about 80%, or from about 50% to about 70%, or from about 50% to about 60%, or from about 60% to about 90%, or from about 60% to about 80%, or from about 60% to about 70%, or from about 70% to about 90%, or from about 70% to about 80%, or from about 30% to about 80%, or from about 30% to about 70%, or from about 30% to about 60%, or from about 30% to about 50%, or from about 30% to about 40%.

Drug loading of nanoparticles that are produced according to any of the methods described herein is, in further embodiments, about 30%, or about 35%, or about 40%, or about 45%, or about 47%, or about 48%, or about 49%, or about 50%, or about 51%, or about 52%, or about 53%, or about 54%, or about 55%, or about 56%, or about 57%, or about 58%, or about 59%, or about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%, The methods disclosed herein, in various embodiments, are contemplated to provide an encapsulation efficiency of from about 50% to about 99%, or from about 60% to about 99%, or from about 70% to about 99%, or from about 80% to about 99%, or from about 90% to about 99%. In further embodiments, the methods disclosed herein are contemplated to provide an encapsulation efficiency of about 50%, about 55%, about 60%, about 65%, about 70%, about 75%, about 80%, about 85%, about 86%, about 87%, about 88%, about 89%, about 90%, about 91%, about 92%, about 93%, about 94%, about 95%, about 96%, about 97%, about 98%, or about 99%. In still further embodiments, the methods disclosed herein are contemplated to provide an encapsulation efficiency of at least about 50%, at least about 55%, at least about 60%, at least about 65%, at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least or about 99%.

Zeta potentials of the formulations were measured by zeta sizer (Agilent, 7030 Nicomp DLS/ZLS-size and zeta, Santa Clara, Calif.) at 23 ° C. Dielectric constant was 78.5.

Spray drying of the nanoparticle suspensions was carried out by integrating the MIVM with a spray dryer (LabPlant, SD-05 Spray Dryer, North Yorkshire, UK). Spray-dry conditions were optimized for the nanoparticles to be re-suspended in aqueous solutions. To prevent the nanoparticles from permanent agglomeration, trehalose (300:1 ratio to the nanoparticles) and leucine (5:1 ratio to the nanoparticles) were added to the nanoparticle suspensions as the excipients during the spray-dry process. Ethanol (60 v/v %) was added in order to lower the inlet temperature of the spray dryer, which was set as 75° C., to compensate the relatively low melting temperature of the polymers. The feed rate of the solutions was 10 mL/min. Spray-dried powders were collected in a glass container at the outlet of the spray dryer. Nanoparticles were resuspended into sterile Millipore water at vigorous stirring for 10 minutes before dosing animals.

Figure 3:
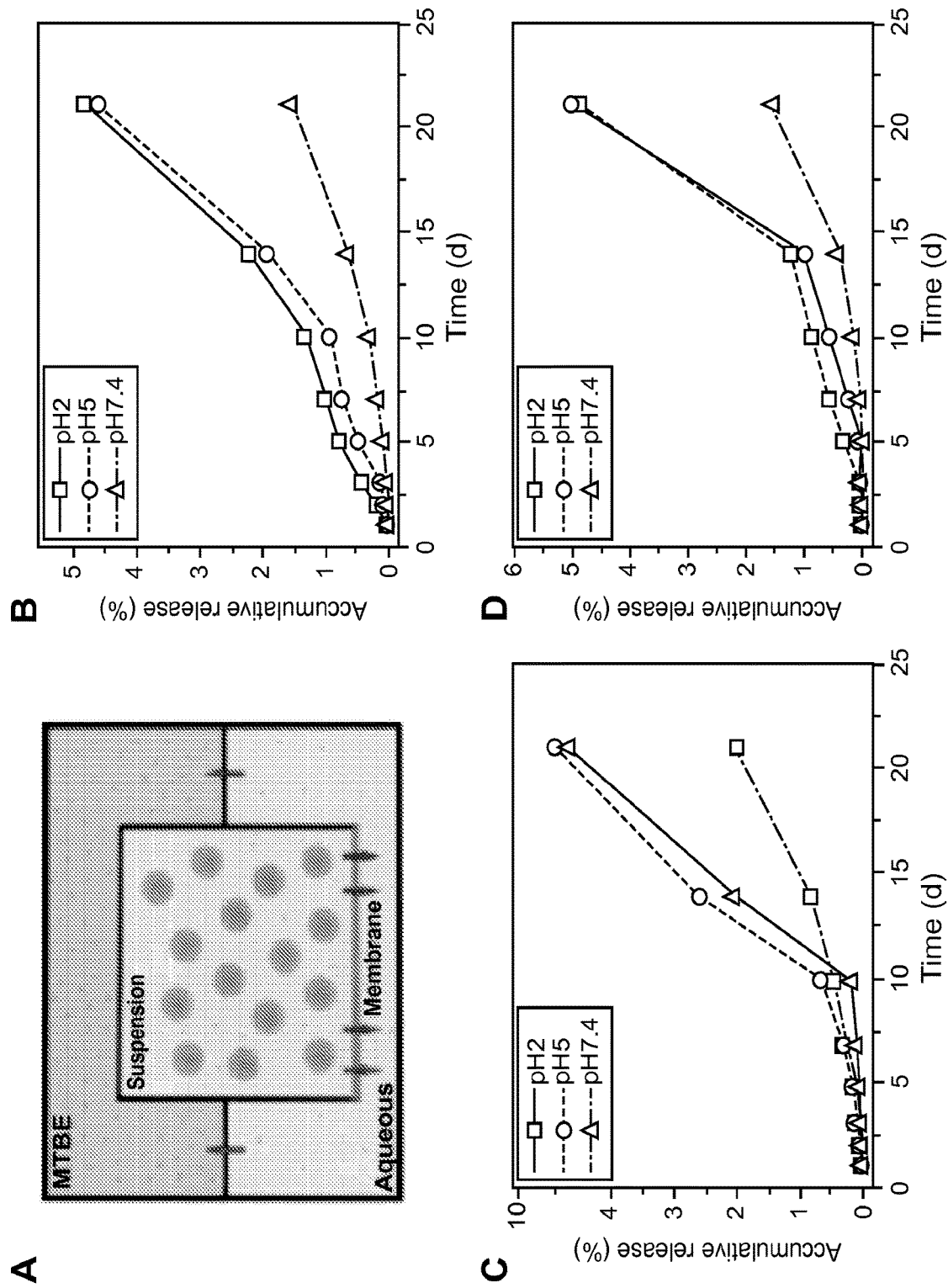
FIG. 3 is illustrates the in vitro release of curcumin from nano-curcumin formulations in a MTBE-aqueous two phase system.
Figure 4:
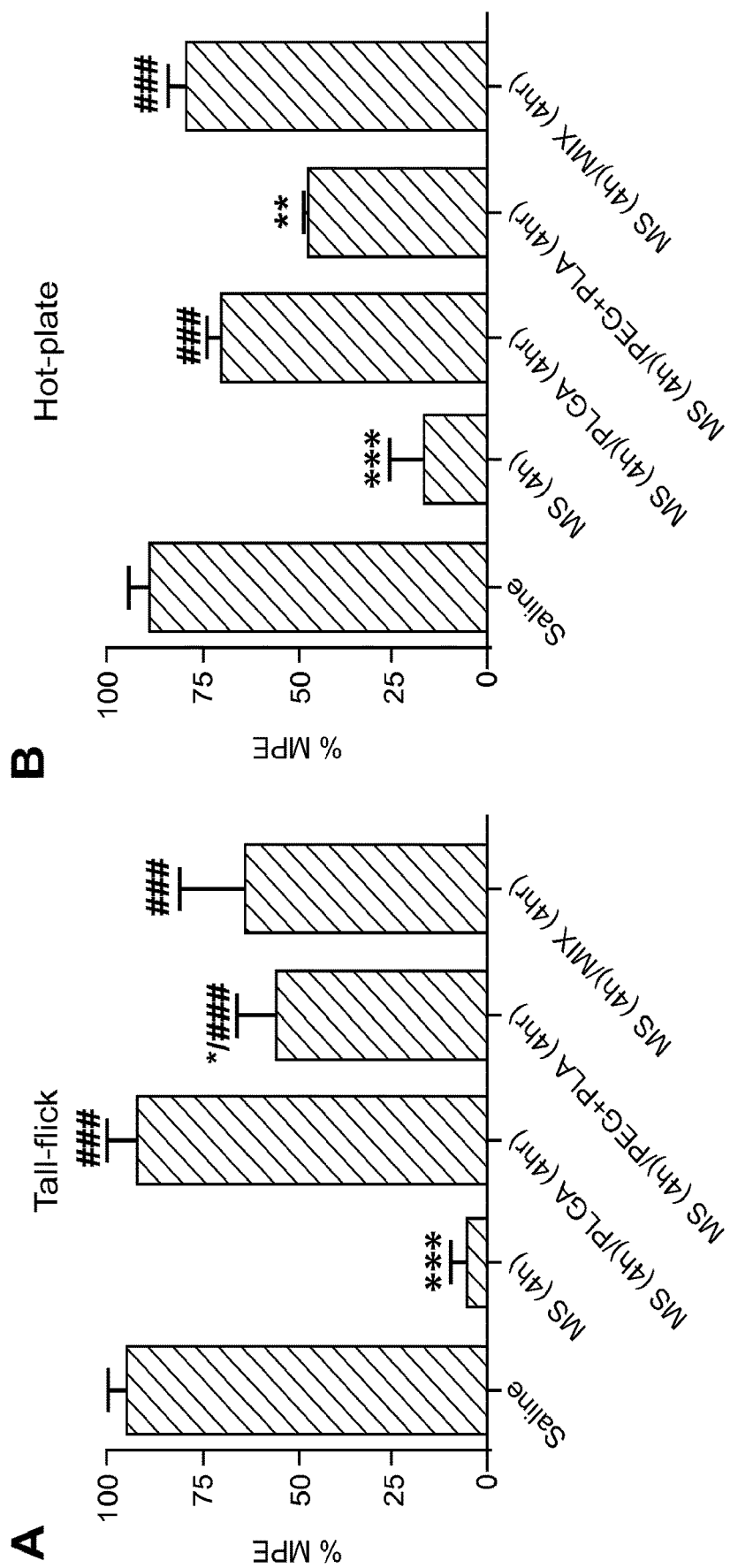
FIG. 4 illustrates the effect of curcumin nanoformulations on morphine tolerance.
Figure 5:
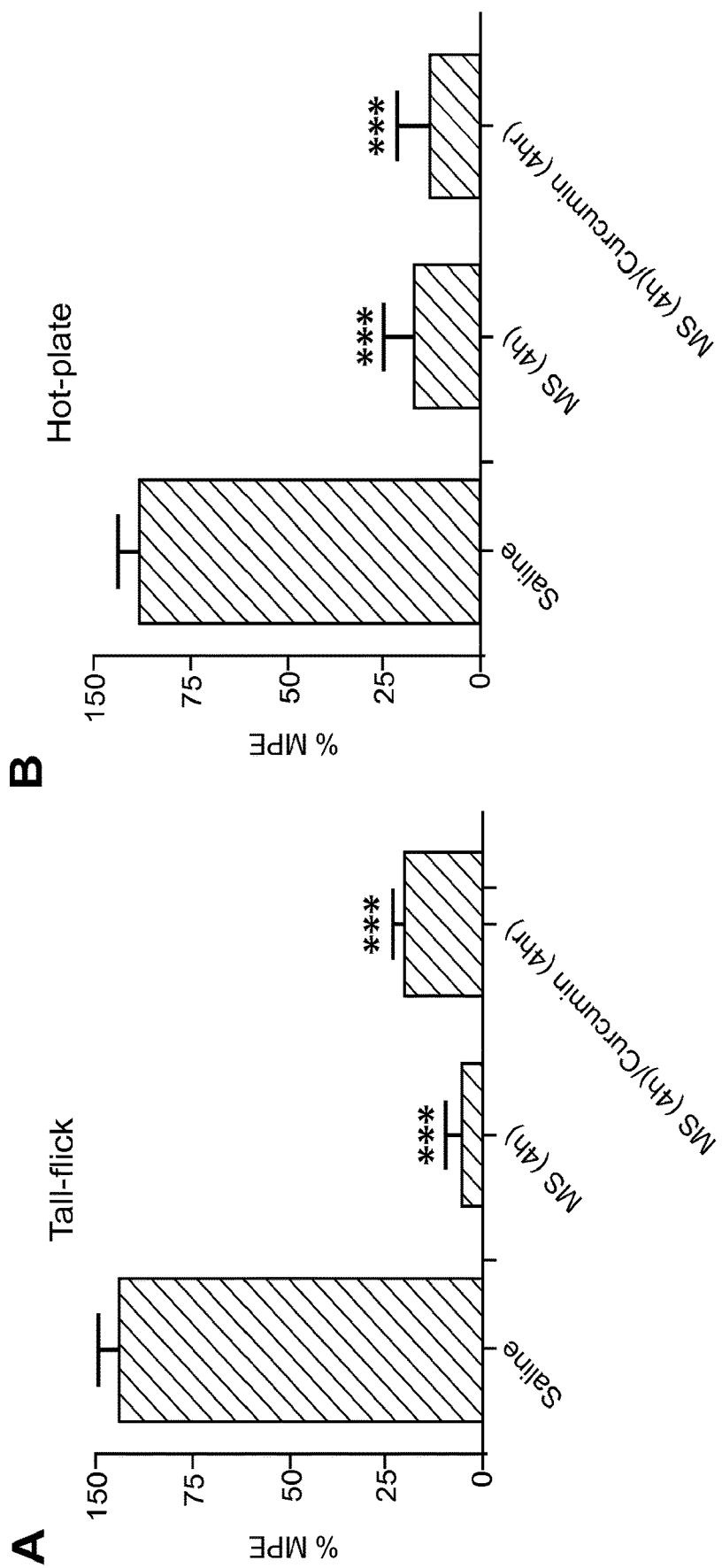
FIG. 5 illustrates the effect of unformulated free curcumin on morphine tolerance.
Figure 6:
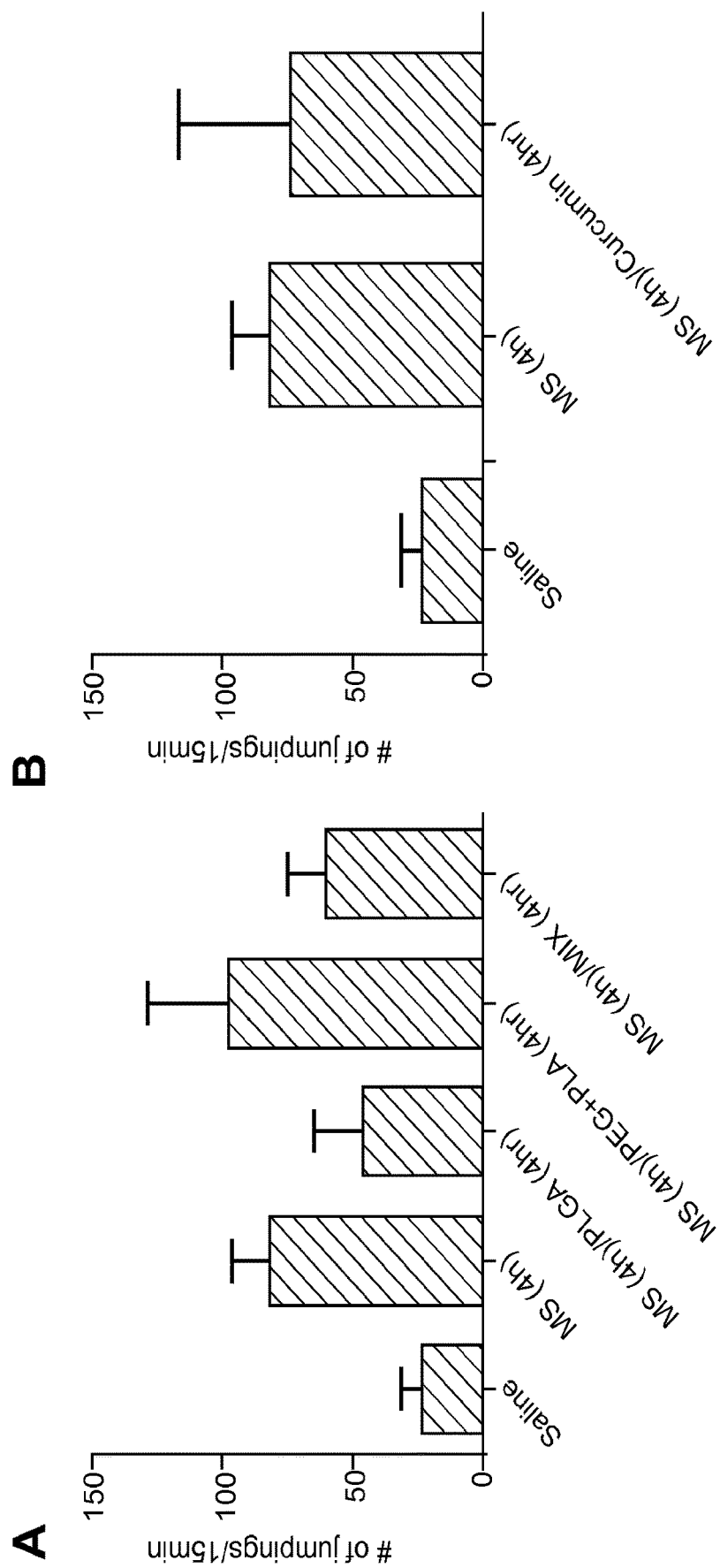
FIG. 6 illustrates the effect of nano-curcumin and curcumin on morphine dependence.

The spray dried PLGA, PEG-b-PLA, and hybrid nanoparticles were resuspended in 0.1 M PBS buffers at pH 2, pH5 and pH7.4 at the concentration of 10 mg/ml for the measurements of curcumin in vitro release. A two-phase system, as shown in FIG. 3A, was designed to overcome the solubility limits of curcumin in aqueous solutions. MTBE was added to the aqueous buffers at 1:2 v/v ratio, which could extract the over saturated curcumin from the aqueous solutions. Solutions (500 µL) were taken from the organic MTBE phase at designed time points (0.5, 1, 2, 4, 6, 24 hours and 2, 3, 5, 7, 14, 21 days) and same amount (500 µL) fresh MTBE were added back to maintain the constant volume of the system. Curcumin in MTBE were quantified using fluorescence plate reader under excitation of 395 nm and emission of 475 nm, respectively.

Male ICR mice (20-25 g, Charles River Laboratories, Wilmington, Mass.) were maintained on a 14/10 h light/dark cycle with access to food and water ad libitum before experimental procedures. All experimental procedures were performed after approval by the Animal Care and Use Committee of the University of Illinois at Chicago and in accordance with the policies and recommendations of the National Institutes of Health guidelines for the handling and use of laboratory animals.

Basal nociception and morphine-induced antinociception were studied using the 52° C. warm-water tail-flick test. In brief, mice were held over the water bath and one third of the distal portion of the tail was immersed into the water. The latency to a quick tail-flick response was recorded as a base-line measurement. Any mouse not responding within 5 sec was excluded from further experiment. To prevent tissue damage, a cut-off time of 12 sec was applied. Morphine-induced antinociception was evaluated 30 min after the injection of a testing dose of morphine (10 mg/kg s.c.), and expressed as the percentage of maximal possible effect (% MPE) according to the following formula:

$$\% \text{ MPE} = 100 \times (\text{postdrug latency} - \text{predrug latency}) / (\text{cut off} - \text{predrug latency})$$

For assessment of response latencies to thermal stimulus in mice, a Cold/Hot Plate Analgesia Meter (Ugo Basile, Comerio, Italy) was used. In this study, mice were placed on a hot plate that was thermostatically maintained at 55±1° C. The nociceptive response was evaluated as the latency to the first licking or lifting of the rear paws or escape jumping. Mice were removed from the hot plate immediately after displaying the response and a cut-off time of 30 sec was set to prevent tissue damage. The anti-nociceptive effect was measured using the same percentage of maximal possible effect (% MPE) as above.

Acute Opioid Tolerance and Dependence

To induce acute tolerance and dependence, separate groups of three ICR mice (20-25 g) were treated with a large dose of morphine (100 mg/kg s.c.). Maximal morphine tolerance and dependence peaked at approximately 4 to 6 h. Mice in the control group received an equal volume of saline. Tolerance to opioids was assessed 4.5 h later by monitoring the antinociceptive effect produced by a test dose of morphine (10 mg/kg, s.c.). The presence of opioid tolerance was signified by a significant reduction of antinociceptive effect. To examine dependence on opioids, mice were challenged with naloxone (10 mg/kg i.p.) 5h after the administration of morphine (100 mg/kg s.c.). Mice were immediately placed inside glass cylinders, and naloxone-induced vertical jumps were recorded for 15 min. To determine the effect of curcumin on preventing acute morphine tolerance and dependence, curcumin was given 15 min before the induction dose of morphine (100 mg/kg s.c.).

Nanoparticle formulations have to meet several requirements to be possibly used for clinical applications (1) all the materials are FDA approved; (2) the process has to be reproducible and scalable; (3) size distribution and surface properties of the nanoparticles have to be well characterized; (4) drug loading of the nanoparticles has to be high enough to contain sufficient active compound at a patient-compliance dose; (5) high encapsulation rate for economic reasons; and (6) better stability and long shelf time more than one year. We have previous developed an integrated process of flash nanoprecipitation and freeze dry to satisfy above requirement. The reactor custom-designed for flash nanoprecipitation provides rapid micromixing to generate nanoparticles with narrow size distribution. Here, all the nanoparticles were generated at high Reynolds number (>9000) to ensure the homogeneous and flash precipitation. PLGA, PEG-b-PLA and hybrid (PLGA to PEG-b-PLA 1:1 molar ratio) nanoparticles encapsulating curcumin were generated to compare the effect of surface properties on drug oral bioavailability and functionality. These polymers are chosen for the study because they are all degradable, biocompatible, and easy to synthesize. Moreover, PLGA and PLA have similar polymer structure with negative charges and PEG brushes were applied to partially or completely shield the surface charges. PEG can prevent non-specific protein absorption and prolong particle blood circulation time.

The average particle size (before and after spray dry), drug loading, encapsulation efficiency, and zeta potential of the nanoparticles with the three polymeric nanoparticle formulations are reported in Table 1. The particles after spray dry are more important, since it represent the particles dosed to animals. After spray dry, the average diameters of all three re-suspended nanoparticles are similar (about 150 nm) with a trend of linearly reduced size when increasing the amount of PEG chains on the surface of the particles, but the difference is within 14% (or 21 nm). Highest drug loading and encapsulation efficiency were found in PEG-b-PLA particles among the three, but the difference is small compared to the PLGA nanoparticles with the lowest drug loading (<3.5%). More than 90% of the drug encapsulation efficiency was found for all three formulations, and PEG-b-PLA nanoparticles presented the highest encapsulation rate. As we expected that with more PEG chains on the surface, zeta potential of the negatively charged PLGA (or PLA) nanoparticles became closer to be neutral.

TABLE 1

Average particle diameter (before and after spray dry), drug loading, encapsulation efficiency of the three curcumin nanoformulations.

| Polymer | Diameter before spray dry (nm) | Diameter after spray dry (nm) | Drug loading (%) | Encapsulation efficiency (%) | Zeta potential (mV) |
|---|---|---|---|---|---|
| PLGA | 79 | 165.8 | 46.2 | 92.4 | −33.1 ± 0.8 |
| PLGA & PEG-b-PLA | — | 159.9 | 47.1 | 94.2 | −24.7 ± 2.9 |
| PEG-b-PLA | 120 | 144.9 | 47.7 | 95.4 | −2.5 ± 1.8 |

Figure 2:
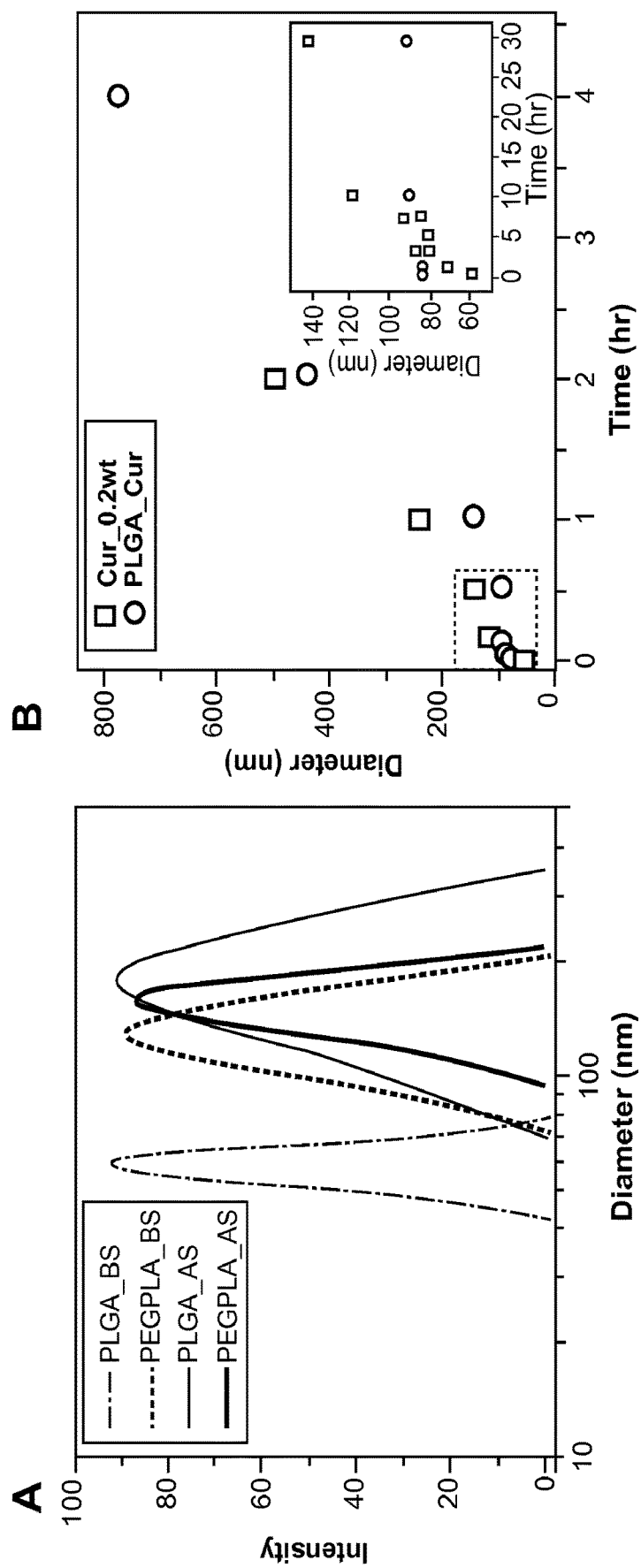
FIG. 2 illustrates the size distributions of PLGA curcumin and PEG-b-PLA curcumin nanoparticles before and after spray dry.

Due to the relatively low glass transition temperature of the PLGA used (~60° C.) high inlet temperature of the spray drier induced active chain motion and resulted in the permanent agglomeration of the particles. Turning now to FIG. 2A, the size of PLGA-curcumin nanoparticles increased from 70 nm to about 165 nm. Dimmers and trimmers were formed during the spray drying process. Also the size distribution after spray drying was boarder compared the size distribution before spray drying. As shown in FIG. 2A, less agglomeration was observed for PEG-b-PLA-curcumin nanoparticles which may be due to the repulsion of PEG brushes.

Pharmacokinetic Study of Orally Administered Nano-Curcumin

Figure 7:
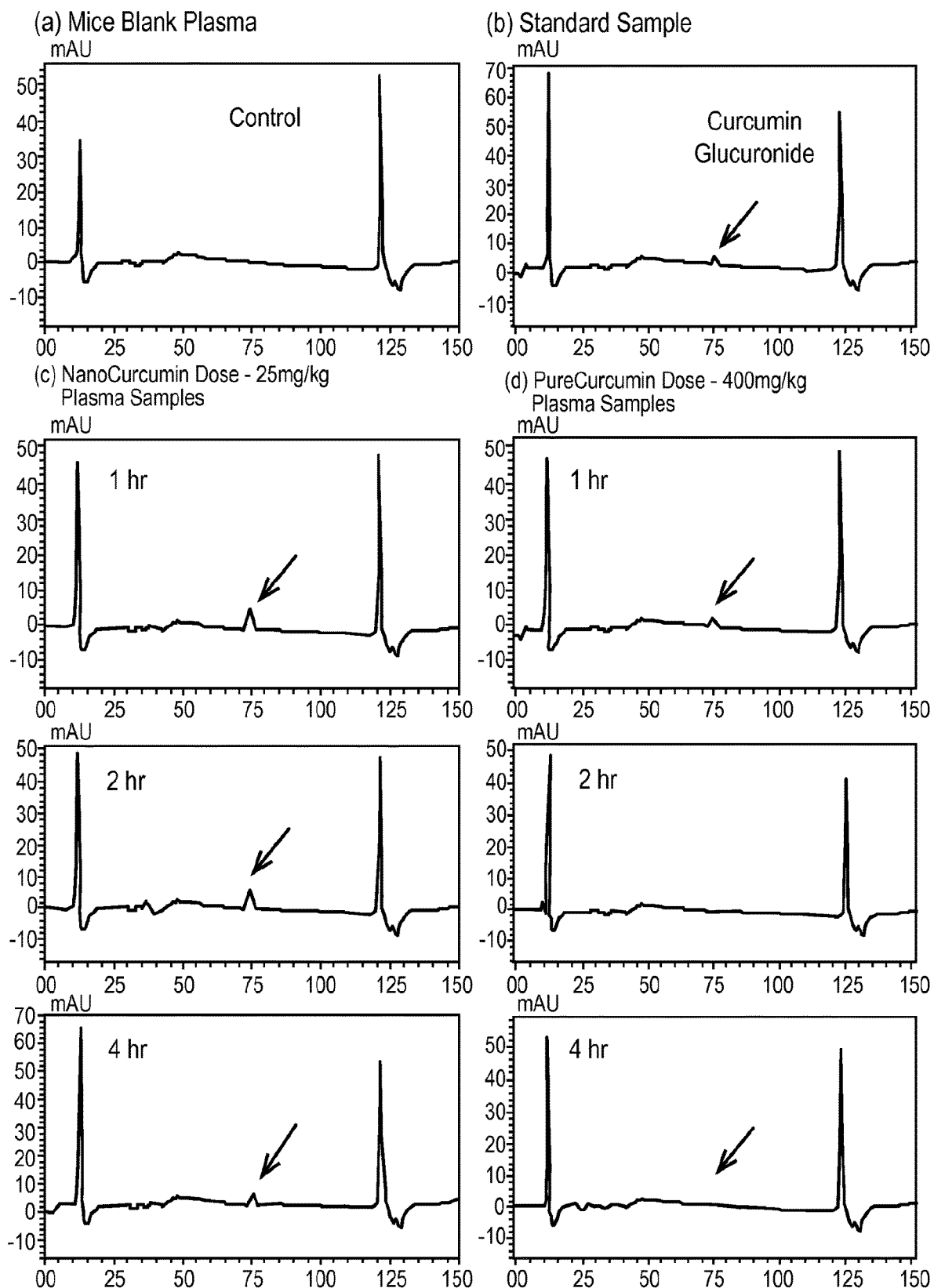
FIG. 7 depicts representative chromatograms of (a) blank rat plasma sample, (b) standard curcumin glucuronide sample, and plasma samples at 1, 2 and 4 hours after oral administration of (c) low-dose nano-curcumin samples and (d) high-dose pure curcumin (in 0.5 wt % methyl cellulose suspension) samples.

The pharmacokinetic study was performed to look at the biodistribution of orally administered nano-curcumin (curcumin or curcumin coencapsulated with piperine in PLGA nanoparticles) at a small dose (25 mg/kg). Unformulated curcumin aqueous suspension at the same dose (25 mg/kg), curcumin aqueous suspension at high dose (400 mg/kg), and curcumin in 0.5% methyl cellulose suspension (to provide better curcumin resuspension) at high dose (400 mg/kg) served as controls. Plasma, brain, and spinal cord tissues were also collected after the oral intake of the aforementioned nano-curcumin and controls. The initial HPLC experiments have shown that the strong UV absorbance peak was found for only nano-curcumin samples when compared with pure curcumin samples at the same dose, indicating better bioavailability. However, the retention time for a curcumin standard was different, indicating the possibility of curcumin metabolism. It was necessary then to perform LCMS to identify the unknown but clearly detectable compound. The LCMS experiments confirmed the presence of curcumin glucuronide, which is considered the most abundant curcumin metabolite after oral delivery of curcumin. The LC/MS chromatograms for curcumin and nano-curcumin samples are presented in FIG. 7. There is a clear indication of an enhanced and prolonged absorption of curcumin glucuronide when using a low dose of nano-curcumin. The high dose of pure curcumin suspended in 0.5% methyl cellulose resulted in a relatively high amount of the metabolite only at 1 hour that was quickly cleared out at later time.

Figure 8:
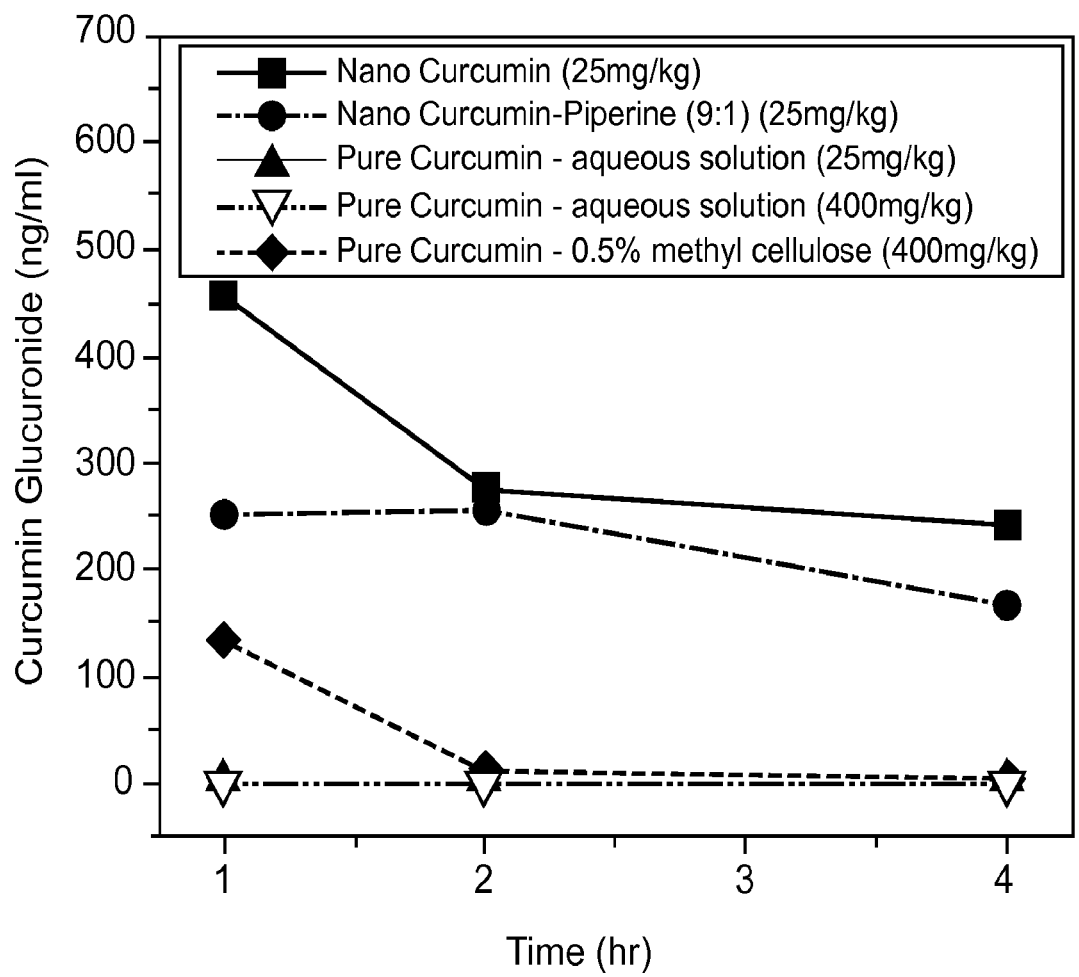
FIG. 8 shows the plasma concentration of curcumin glucuronide after oral administration in mice.

The quantification of curcumin/curcumin glucuronide was performed by a very sensitive and validated LC/MS method. The results were directly obtained and extrapolated on the calibration curve. The calibration lines were shown to be linear from 2 ng/ml to 1000 ng/ml ($r^2$=0.9981) and 0.5 ng/ml to 250 ng/ml ($r^2$=0.9980) for curcumin glucuronide and curcumin, respectively. FIG. 8 illustrates the concentration versus time profiles for curcumin glucuronide after oral administration of formulated and unformulated curcumin at low and high doses. The data indicated an enhanced bioavailability of curcumin glucuronide for nano-curcumin samples when compared with the unformulated ones.

Figures 1, 9:
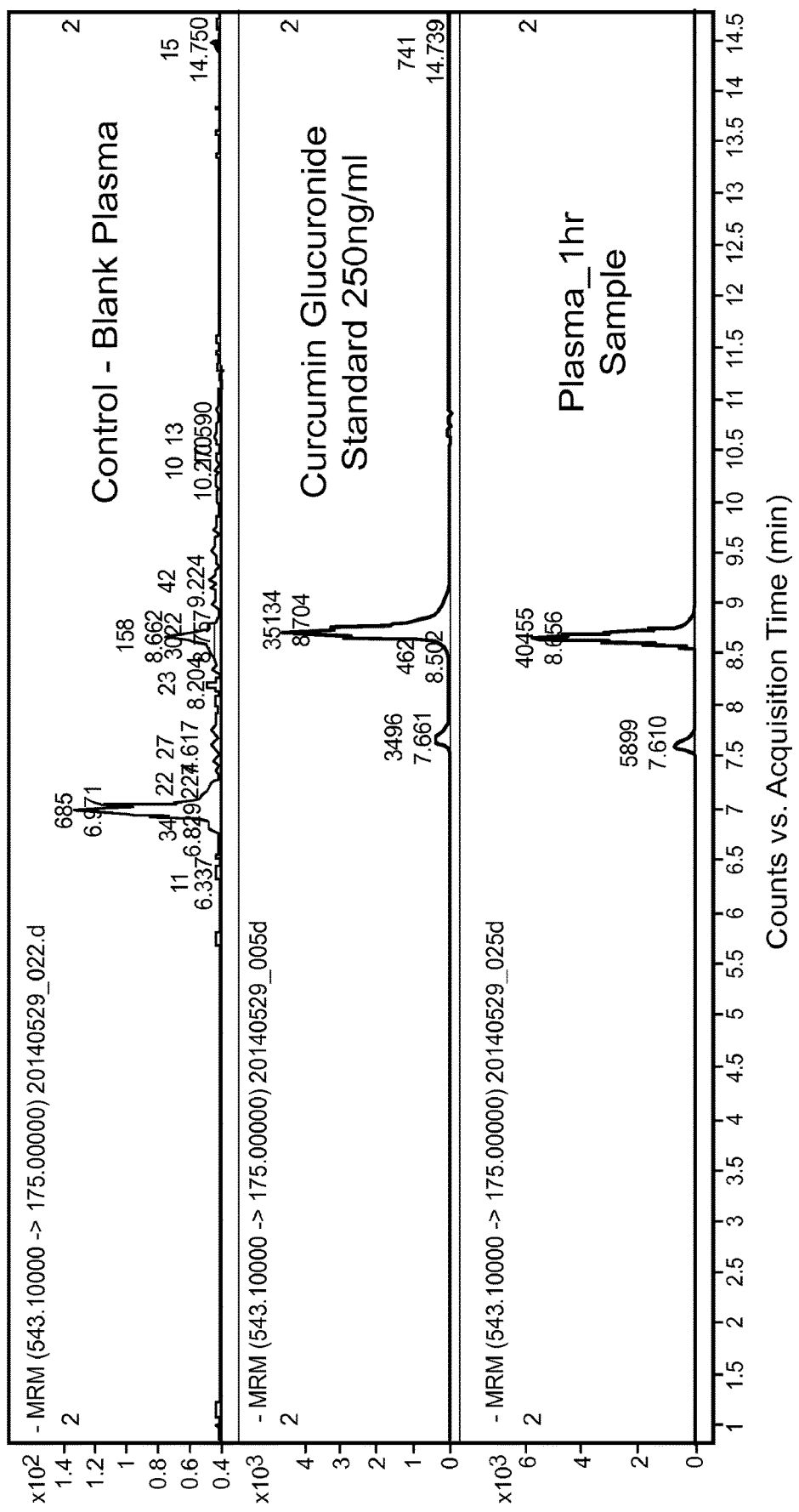
FIG. 9 depicts typical LCMS/MS chromatograms of curcumin glucuronide for (a) blank plasma, (b) standard solution, (c)-(e) 1 hour, 2 hour, 4 hour in vivo plasma samples after oral administration of low dose (25 mg/kg) curcumin nanoparticles.
Figures 2, 9:
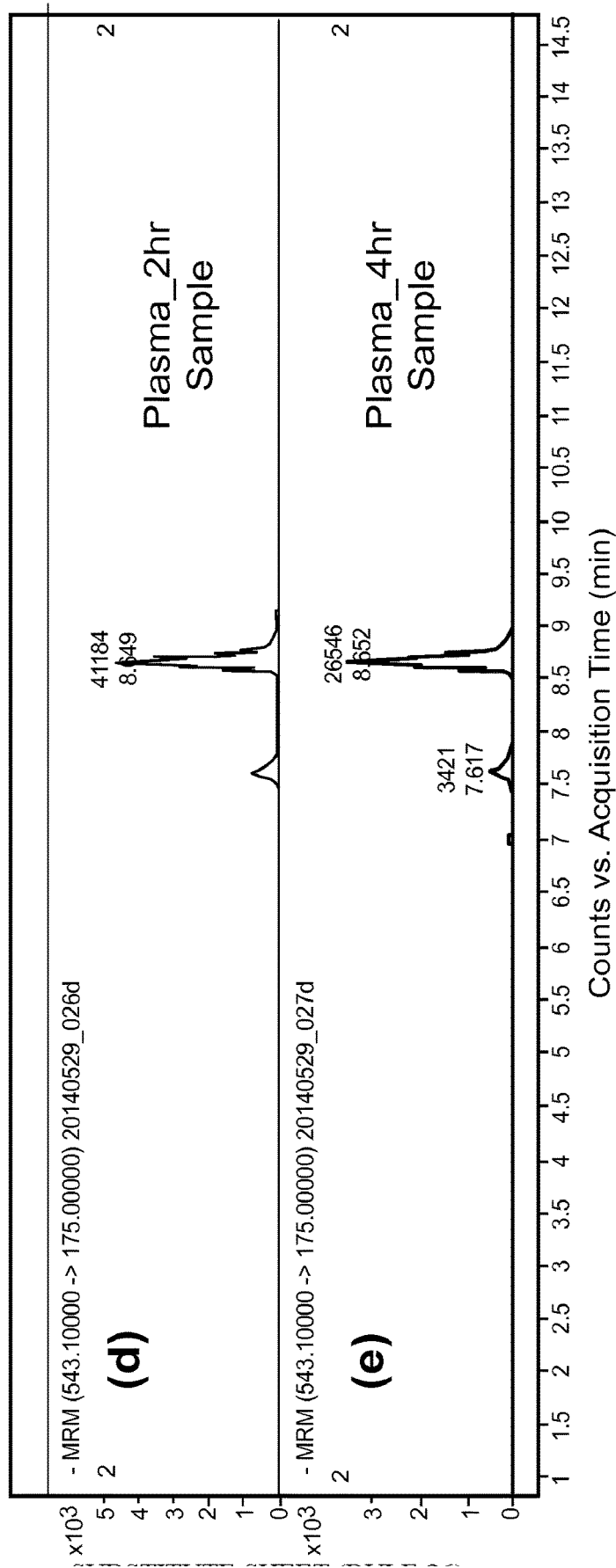

The typical chromatograms obtained for the LC/MS measurements for quantification of curcumin glucuronide are presented in FIG. 9. They clearly indicate the assay specificity, as there was not endogenous plasma components eluted at the retention time of curcumin glucuronide.

The pharmacokinetic study also indicated that free curcumin was only detectable (at very low concentration) in plasma samples after oral delivery of curcumin-piperine (9:1) nanoparticles (Table 1). Furthermore, the quantities of curcumin/curcumin glucuronide present in brain and spinal cord were also below the detection limit of the instrument.

TABLE 1

Trace concentrations of native curcumin detected in plasma after oral administration of Curcumin-Piperine (9:1) Nanoparticle at 25 mg/kg dose.

| Time (hr) | Concentration (ng/ml) |
|---|---|
| 1 | 0.655 |
| 2 | 0.685 |
| 4 | 0 |

Figure 10C:
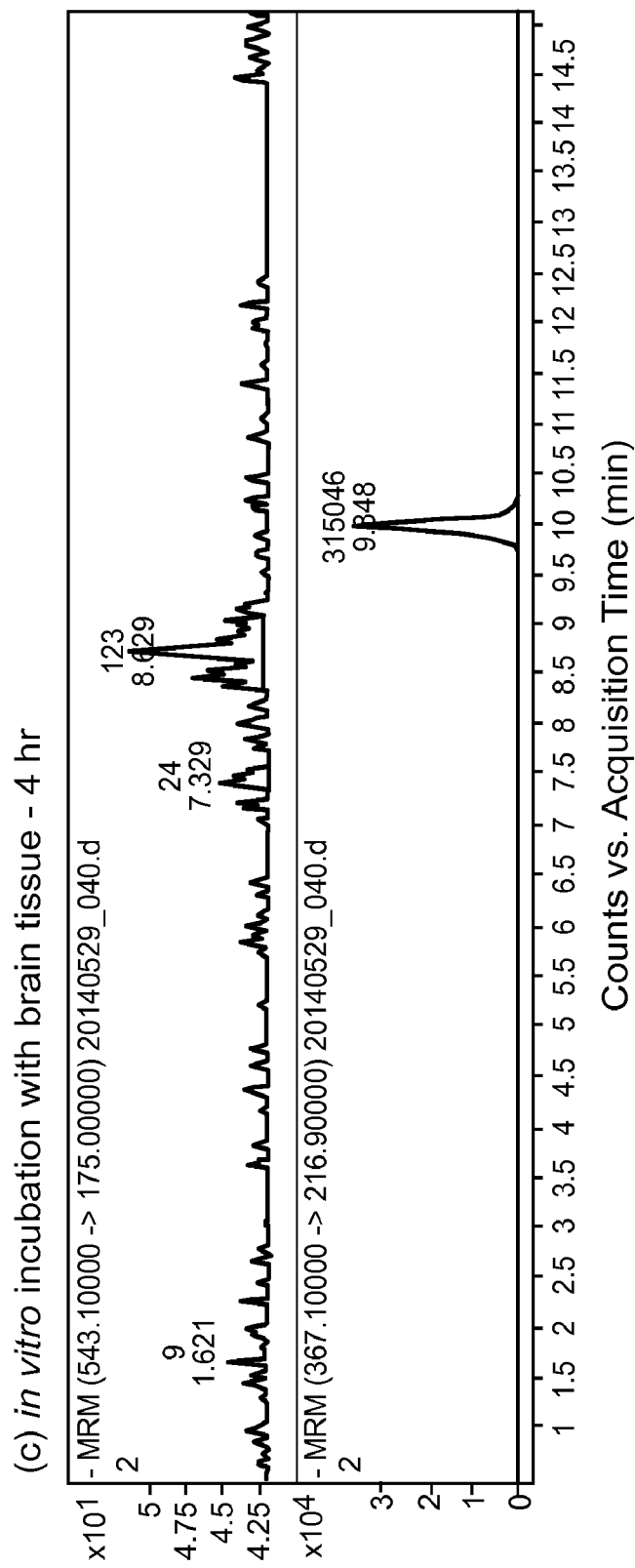
FIG. 10 shows control in vitro experiments for incubation of curcumin nanoparticles in (b) plasma and (c) brain tissue.

The control in vitro experiments were performed to test the stability of curcumin after incubation of curcumin nanoparticle suspension in plasma and brain tissue at 1 hour, 2 hour, and 4 hour time point. The LC/MS MRM chromatograms for the sample at 4 hours (FIG. 10) clearly show that the incubation of curcumin did not cause any drug biotransformation or metabolism. Both the plasma and brain tissues samples contained native curcumin only.

Additional Compositions

In addition to curcumin, a nanoparticle composition may be formed wherein the hydrophobic compound may be selected from the group consisting of at least one of any tobramycin, digoxin, estrone, glyburide, metformin, and doxorubicin.

It should be noted that various changes and modifications to the presently preferred embodiments described herein will be apparent to those skilled in the art. Such changes and modifications may be made without departing from the spirit and scope of the present invention and without diminishing its attendant advantages.

What is claimed is:

1. A continuous method for producing a nanoparticle with increased bioavailability in a reactor comprising:
   a. dissolving curcumin and poly(lactic-co-glycolic acid) (PLGA) in an organic solvent wherein the ratio of the at least one curcumin to PLGA is at least 1:2, and wherein the curcumin and PLGA are in the same inlet stream of the reactor;
   b. mixing the resultant mixture in the organic solvent with one or more antisolvent(s) to produce the nanoparticle, wherein the nanoparticle is generated at a mixing time of 1.5 milliseconds or less, or at a Reynolds number of at least about 9,000;
   c. adding an additive to the same stream as the mixture wherein the weight ratio of additive to nanoparticle is at least 1:1; and
   d. drying the mixture, wherein the resulting nanoparticle has increased bioavailability.

2. The method of claim 1, wherein the nanoparticle further comprises a marker.

3. The method of claim 2, wherein the marker is a fluorescent dye, an organic or inorganic dye, an inorganic nano-crystal/particle, or a colloid.

4. The method of claim 1, further comprising resuspending the nanoparticle in an aqueous or in an organic solution.

5. The method of claim 1, wherein the additive is selected from the group consisting of a sugar-type molecule, a sugar alcohol, an amino acid, a surfactant, polyvinyl alcohol, and polyvinylpyrrolidone.

6. The method of claim 5, wherein the sugar-type molecule is glucose, fructose, trehalose, sucralose, or lactose.

7. The method of claim 5, wherein the sugar alcohol is glycerol, lactitol, xylitol, or sorbitol.

8. The method of claim 5, wherein the amino acid is leucine, lysine, glycine, threonine, or valine.

9. The method of claim 5, wherein the surfactant is a fatty acid, a lipopeptides, or a glycolipid.

10. The method of claim 5, wherein the weight ratio of additive to nanoparticle is from about 1:1 to about 300:1.

11. A scalable and continuous method for manufacturing stable polymeric nanoparticles encapsulating curcumin comprising:
    a. dissolving curcumin and poly(lactic-co-glycolic acid) (PLGA) in one or more organic solvents wherein the curcumin and PLGA are in the same inlet stream of a reactor, and
    b. mixing the resultant mixture in the one or more organic solvent(s) with one or more antisolvent(s) to form nanoparticles, wherein the nanoparticle is generated at a mixing time of 1.5 milliseconds or less, or at a Reynolds number of at least about 9,000, and wherein the resulting nanoparticle has increased bioavailability.

12. The method of claim 11 further comprising steps of nanoparticle characterization, spray drying or freeze drying, and re-suspension.

13. The method of claim 11 wherein at least one marker is used.

14. The method of claim 11, wherein the nanoparticles are about 50 nanometers (nm) to about 300 nm in mean diameter.

15. The method of claim 1 wherein the mixing of step (b) is 1.5 milliseconds or less.

16. the method of claim 1 wherein the drying is spray drying or freeze drying.

17. The method of claim 11 wherein the mixing of step (b) is 1.5 milliseconds or less.

18. the method of claim 11 wherein the drying is spray drying or freeze drying.

* * * * *